(12) United States Patent
Godfrey et al.

(10) Patent No.: US 10,416,107 B2
(45) Date of Patent: Sep. 17, 2019

(54) CONDUCTIVITY SENSOR WITH VOID CORRECTION

(71) Applicant: Ecolab USA Inc., St. Paul, MN (US)

(72) Inventors: Martin Ray Godfrey, Eagan, MN (US); Eugene Tokhtuev, Duluth, MN (US); Joseph Erickson, Cloquet, MN (US)

(73) Assignee: Ecolab USA Inc., Saint Paul, MN (US)

( * ) Notice: Subject to any disclaimer, the term of this patent is extended or adjusted under 35 U.S.C. 154(b) by 92 days.

(21) Appl. No.: 15/242,132

(22) Filed: Aug. 19, 2016

(65) Prior Publication Data

US 2018/0052133 A1 Feb. 22, 2018

(51) Int. Cl.
*G01N 27/08* (2006.01)
*G01N 27/22* (2006.01)
(Continued)

(52) U.S. Cl.
CPC ......... *G01N 27/228* (2013.01); *G01N 27/025* (2013.01); *G01N 27/08* (2013.01); *G01N 27/226* (2013.01); *G01N 27/07* (2013.01)

(58) Field of Classification Search
CPC ........ G01D 5/24; G01D 5/241; G01D 5/2412; G01D 5/2417; G06K 9/0002; G01R 27/26;
(Continued)

(56) References Cited

U.S. PATENT DOCUMENTS

| 4,132,944 A | * | 1/1979 | Bentz | ..................... G01N 27/02 324/441 |
| 4,482,967 A | * | 11/1984 | Evans, Jr. | .............. G01N 27/06 702/30 |

(Continued)

FOREIGN PATENT DOCUMENTS

| EP | 0308004 A2 | 3/1989 |
| GB | 2529538 A | 2/2016 |

OTHER PUBLICATIONS

International Patent Application No. PCT/US2017/047415, International Search Report and Written Opinion dated Nov. 14, 2017, 14 pages.
(Continued)

*Primary Examiner* — Patrick Assouad
*Assistant Examiner* — Demetrius R Pretlow
(74) *Attorney, Agent, or Firm* — Fredrikson & Byron, P.A.

(57) ABSTRACT

Systems and methods can be used for correcting for the presence of voids in a fluid when measuring the conductivity thereof. The conductivity of a fluid can be measured using a conductivity sensor. Capacitance electrodes can be used to measure the capacitance of the fluid. The measured capacitance affected by the fluid can be used in combination with the measured conductivity to determine a corrected conductivity value that compensates for possible voids in the fluid. Other parameters, such as the makeup or temperature of the fluid can be used in determining the corrected conductivity
(Continued)

measurement. Some such systems include an annular housing and can be inserted or integrated into fluid flow systems so that fluid to be analyzed flows through an aperture defined by the annular housing.

21 Claims, 10 Drawing Sheets

(51) Int. Cl.
G01N 27/02 (2006.01)
G01N 27/07 (2006.01)

(58) Field of Classification Search
CPC ............ G01R 27/2605; H03K 17/955; H03K 2217/960725; G06F 3/0414; G06F 2203/04103; G01N 27/08; G01N 27/288; G01N 27/025; G01N 27/226; G01N 27/07
USPC ....... 324/600, 649, 658, 663, 669, 670, 684, 324/685, 686, 691, 693, 718, 720, 721, 324/722; 345/173, 174; 702/47, 52
See application file for complete search history.

(56) References Cited

U.S. PATENT DOCUMENTS

| 4,717,582 | A | 1/1988 | Kotoye et al. |
|---|---|---|---|
| 5,077,525 | A | 12/1991 | West et al. |
| 5,589,642 | A | 12/1996 | Agar et al. |
| 5,597,950 | A | 1/1997 | Mullen |
| 5,741,977 | A | 4/1998 | Agar et al. |
| 6,078,729 | A | 6/2000 | Kopel et al. |
| 6,414,493 | B1 | 7/2002 | Rezvani |
| 6,823,271 | B1 | 11/2004 | Foss |
| 7,126,343 | B1 | 10/2006 | Howes, Jr. et al. |
| 7,201,068 | B2 | 4/2007 | Foss et al. |
| 7,842,348 | B2 | 11/2010 | Abbott et al. |
| 7,878,703 | B2 | 2/2011 | Roberts |
| 9,410,910 | B1 | 8/2016 | Fougere |
| 2004/0012395 | A1 | 1/2004 | Salamitou |
| 2007/0024287 | A1* | 2/2007 | Graves ................... G01N 27/06 324/453 |
| 2008/0262748 | A1* | 10/2008 | Ossart ................... G01N 27/221 702/21 |
| 2009/0160461 | A1* | 6/2009 | Zangl ....................... G01D 5/24 324/684 |
| 2010/0188111 | A1* | 7/2010 | Fougere ................. G01N 27/02 324/698 |
| 2010/0327884 | A1* | 12/2010 | McCall ................. F01N 3/2066 324/682 |
| 2011/0316563 | A1* | 12/2011 | Davies ................. G01N 27/221 324/663 |
| 2012/0058025 | A1* | 3/2012 | Fienup ................... A47L 15/44 422/261 |
| 2014/0152332 | A1* | 6/2014 | Platte ..................... G01N 27/06 324/713 |
| 2015/0002178 | A1* | 1/2015 | Herb ...................... G01N 27/02 324/693 |

OTHER PUBLICATIONS

"Flow Through Toroidal Conductivity Sensor," Rosemount Analytical, Production Data Sheet, Model 242, PDS 71-242/rev.D, Apr. 2004, 8 pages.

* cited by examiner

CONDUCTIVITY SENSOR WITH VOID CORRECTION

BACKGROUND

Fluid conductivity measurements are used in a widespread number of applications. In various implementations, conductivity measurements can be used to determine the concentration of a constituent in the fluid being analyzed. In other cases, the conductivity of the fluid itself can be an important parameter for various uses of the fluid, such as requiring a fluid be sufficiently conductive or sufficiently insulating.

Various conductivity measuring devices have been developed. For example, contact sensors including one or more electrodes in communication with the fluid can be used to analyze the fluids electrical characteristics. In other examples, toroidal sensors can be used for measuring the conductivity of a fluid flowing through the center of the toroid.

Such sensors generally operate under the assumption that only the fluid is contributing to the measured conductivity of the fluid. However, in some cases, voids (e.g., air bubbles) trapped in the fluid can undesirably affect the sensor's ability to measure the conductivity. That is, the voids in the fluid often have different electrical characteristics than the fluid itself. The presence of such voids (e.g., flowing through toroidal sensors or contacting electrodes) can therefore skew the conductivity measurement so that the measured conductivity unpredictably represents the conductivities of the both the fluid and the void in an unknown instantaneous combination.

In some examples, the conductivity measurement is used to determine the concentration of one or more chemical species in a fluid. However, the chemical species itself may facilitate the formation of voids in the form of bubbles or foam in the fluid. Exemplary fluids in which this may occur include cleaning, washing, and sanitizing solutions. Thus, such bubbles or foam formed in such solutions can negatively impact the ability to measure the conductivity, and therefore, in some cases, a concentration, of the solution.

SUMMARY

Some aspects of the disclosure are generally directed toward system and methods for measuring conductivity of a fluid and correcting for voids in the fluid. Systems can include a conductivity sensor for measuring the conductivity of a portion of the fluid. Systems can further include first and second capacitance electrodes and a controller configured to determine a measured conductivity from the conductivity sensor and a measured capacitance between the first and second capacitance electrodes. The controller can be configured to determine a corrected conductivity measurement based on the measured capacitance and the measured conductivity.

In some examples, determining the corrected conductivity measurement can be based on other data in addition to the measured conductivity and the measured capacitance. For example, in some cases, the relationship between the capacitance and the correction to the conductivity measurement can be based on the type of fluid flowing in the system, which can be entered, for example, via a user interface. Additionally or alternatively, the relationship between the measured capacitance and the correction to the conductivity measurement can be temperature dependent. Thus, the system can include a temperature sensor for determining the temperature of the fluid in order to determine the corrected capacitance.

In an exemplary configuration the system includes a sensor assembly which includes the first and second capacitance electrodes. The sensor assembly can include an annular housing having an inner surface and an outer surface, wherein the inner surface defines an aperture. The conductivity sensor can include a first coil positioned in the annular housing and surrounding the inner surface. A second coil can be similarly positioned in the annular housing surrounding the first coil and downstream from the first coil. The first and second coils can be used to measure the conductivity of the fluid that flows through the aperture defined by the inner surface of the annular housing. In some such examples, the first and second capacitance electrodes can be positioned proximate the inner surface of the annular housing so that the fluid flowing therethrough affects the capacitance between the first and second capacitance electrodes.

Such systems can be integrated into fluid flow systems in a variety of ways. In some embodiments, the annular housing can be inserted into a tee-pipe in a fluid flow system so that the fluid flowing in the system flows through the aperture in the annular housing. In other examples, the system can include flanges on either side of the annular housing configured to interface with fluid flow vessels in the fluid flow housing. The flanges can interface with such vessels so that the vessels and the annular housing combine to create a fluid flow path therethrough.

Methods can include flowing a fluid sample past a conductivity sensor and measuring the conductivity of the fluid. Methods can further include flowing the fluid sample past first and second capacitance electrodes and measuring a capacitance affected by the fluid sample using the first and second capacitance electrodes. Still further, methods can include correlating the measured capacitance with a conductivity correction and calculating a corrected conductivity by adjusting the measured conductivity based on the conductivity correction.

Such systems and methods can be implemented to measure the conductivity of and a capacitance affected by approximately the same volume of fluid. In various examples, this can include positioning the capacitance electrodes and the conductivity sensor so that the measured conductivity and the measured capacitance are affected by approximately the same portion of fluid and the conductivity and capacitance are measured substantially simultaneously. In other examples, the conductivity sensor can be positioned upstream or downstream from the capacitance electrodes by a known distance. The conductivity and capacitance measurements can be temporally offset based on the distance between the conductivity sensor and the capacitance electrodes so that the portion of fluid affects the conductivity and capacitance measurements.

DETAILED DESCRIPTION

Figure 1:
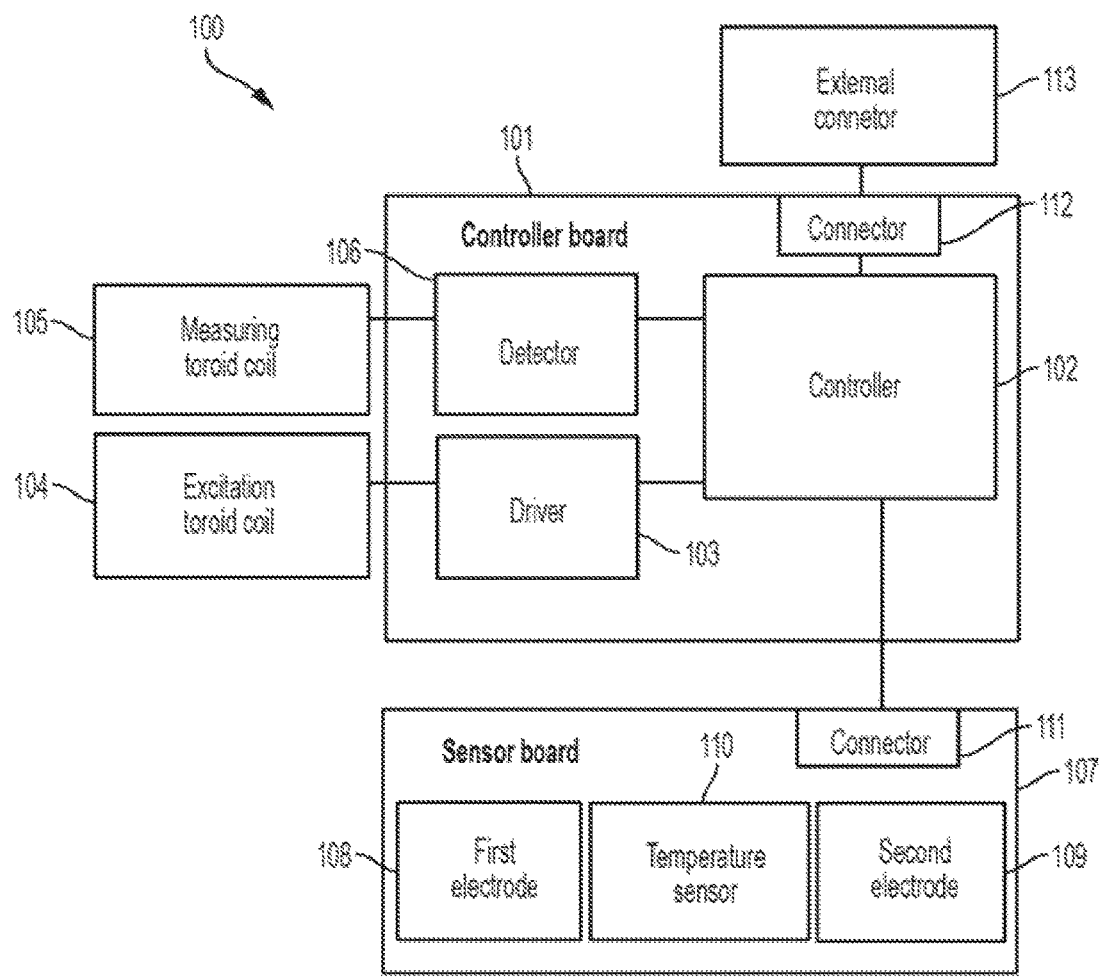
FIG. 1 is a block diagram illustrating an exemplary electrical schematic for a conductivity sensor with void correction.

FIG. 1 is a block diagram illustrating an exemplary electrical schematic for a conductivity sensor with void correction. In the illustrated embodiment, the sensor 100 includes an excitation toroid coil 104 and a measuring toroid coil 105, which can be used to inductively determine the conductivity of a fluid flowing through the toroid coils. The sensor includes a controller 102, which can be configured to drive the excitation toroid coil 104 via a driver 103, such as causing an excitation current to flow through the excitation toroid coil. The controller 102 can be further configured to receive a signal representative of the current flowing through the measuring toroid coil 105 via detector 106. The use of excitation and measuring toroid coils to inductively measure the conductivity of a fluid is described, for example, in U.S. Pat. No. 7,126,343, filed Jul. 27, 2005, which is assigned to the assignee of the instant application and is incorporated herein by reference in its entirety. However, it will be appreciated that, while used as an illustrative example, sensors within the scope of this disclosure need not be limited to inductive conductivity measurements such as by methods incorporating such toroid coils. Rather, other known conductivity sensing techniques may be used in addition to or instead of the driver 103, excitation toroid coil 104, measuring toroid coil 105, and detector 106. In general, the controller 102 can interface with coils 104, 105 or with other conductivity sensing devices to receive a signal indicative of the conductivity of a sample fluid.

As shown in FIG. 1, the sensor 100 includes a sensor board 107 in communication with the controller 102 via a connector 111. The sensor board includes a first electrode 108, and a second electrode 109. The first 108 and second 109 electrodes can be used, for example, as capacitance electrodes. That is, the controller 102, via connector 111, can determine the capacitance between the first 108 and the second 109 electrodes. The sensor board of FIG. 1 further includes a temperature sensor 110, which can be used to monitor a temperature, for example, the temperature of an object proximate or between the first 108 and second 109 electrodes. Temperature sensor 110 can include any appropriate temperature sensor, such as a thermocouple, thermistor, and the like. It will be appreciated that, while shown as a physical connection, in some embodiments, connector 111 can facilitate wired and/or wireless communication between elements of the sensor board 107 and the controller 102.

As shown, the controller 102 can communicate with an external connector 113 via connector 112 on the controller board. In various embodiments, connector 112 and external connector 113 can be in wired or wireless communication. In some examples, external connector 113 can interface with various system components, such as a system controller configured to interact with other portions of a fluid flow system. For instance, external connector 113 can interface with a computer or control center capable of performing analysis on the received data and executing processes affecting the fluid under analysis. For example, a control device receiving data via the external connector 113 may adjust the fluid based on the measured conductivity of the fluid, such as increasing or decreasing the concentration of a fluid component in order to adjust the conductivity. Adjusting the fluid can include, for example, adjusting the concentration of a fluid component, the flow rate of the fluid, the temperature of the fluid, or other fluid properties. Additionally or alternatively, the external connector 113 can be in communication with external sensors that can provide data to the controller 102. For example, in some embodiments, the controller 102 can be in communication with a flow meter configured to measure the flow rate of fluid through the sample. Flow rate data can be used to track the location of a particular volume of fluid through the system.

Figure 2B:
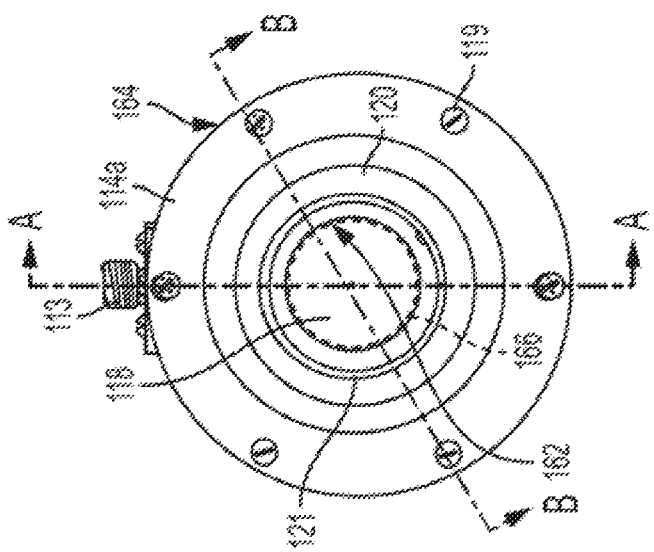
FIGS. 2A and 2B are front and side views, respectively, of an exemplary conductivity sensor integrated into a section of pipe.
Figure 2A:
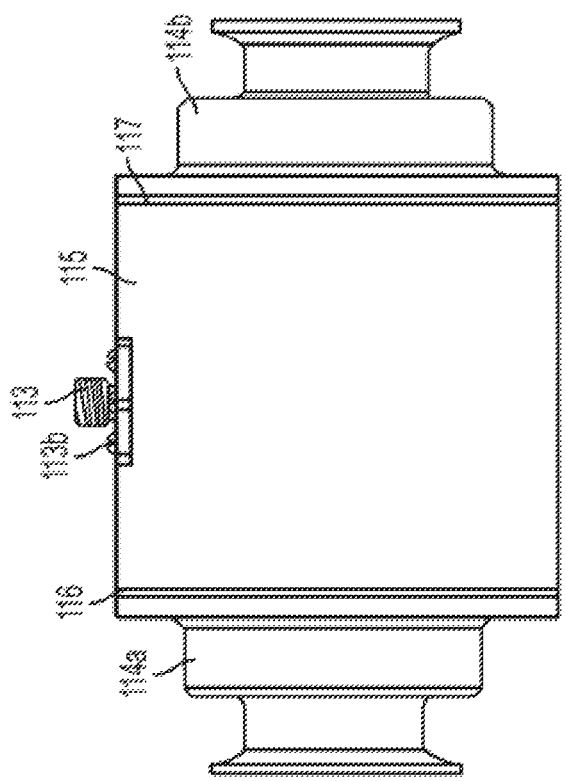

FIG. 2A is a front view of an exemplary conductivity sensor integrated into a section of pipe. In the illustrated embodiment of FIG. 2A, the conductivity sensor 100 is embodied as a section of pipe to place in the flow line of a fluid flow system. As shown, the sensor includes a housing 115 surrounding and substantially enclosing sensor components. The conductivity sensor 100 of FIG. 2A includes an external connector 113 similar to that discussed above with respect to FIG. 1. In the illustrated embodiment, the external connector 113 is secured to the housing 115 via screws 113b.

The housing 115 is positioned adjacent to flanges 114a and 114b to facilitate adjoining the conductivity sensor 100 to fluid flow vessels in fluid flow systems. While shown in the illustrated example as comprising 3A sanitary connections, it will be appreciated that any appropriate connection type for connecting to a fluid flow vessel in a fluid flow assembly is possible. Gaskets 116 and 117 can be positioned between the housing and the flanges 114a and 114b, respectively, to provide a seal at the seam. Flanges 114a, 114b along with an internal section of the sensor 100 define a flow path for fluid flowing through the sensor 100.

FIG. 2B is a side view of the conductivity sensor of FIG. 2A. The sensor 100 includes a flow path 118 extending through the flange 114a and into the interior of the sensor 100. One or more screws 119 about the perimeter of the sensor can be used to secure flange 114a to the housing 115 and to compress the gasket 116 between the flange 114a and the housing 115. For example, in some examples, a plurality of screws or other fasteners (e.g., bolts, etc.) can be substantially equally spaced out about the perimeter of the flange 114a to evenly compress the gasket 116 between the flange 114a and the housing 115. Similarly, one or more screws or other fasteners can be used to secure flange 114b to the housing 115 and to compress the gasket 117 between the flange 114b and the housing 115. The housing 115, including the inner diameter of the flow path 118, defines an annular housing having an outer surface 164 and an inner surface 162. The inner surface defines an aperture 166 corresponding to the flow path 118 through the sensor 100.

In the illustrated embodiment, the 3A sanitary connection on flange 114a includes a clamp connection 120 in order to connect the connection to a corresponding connection on an adjacent connection, such as on a pipe in a fluid flow system.

Figure 3A:
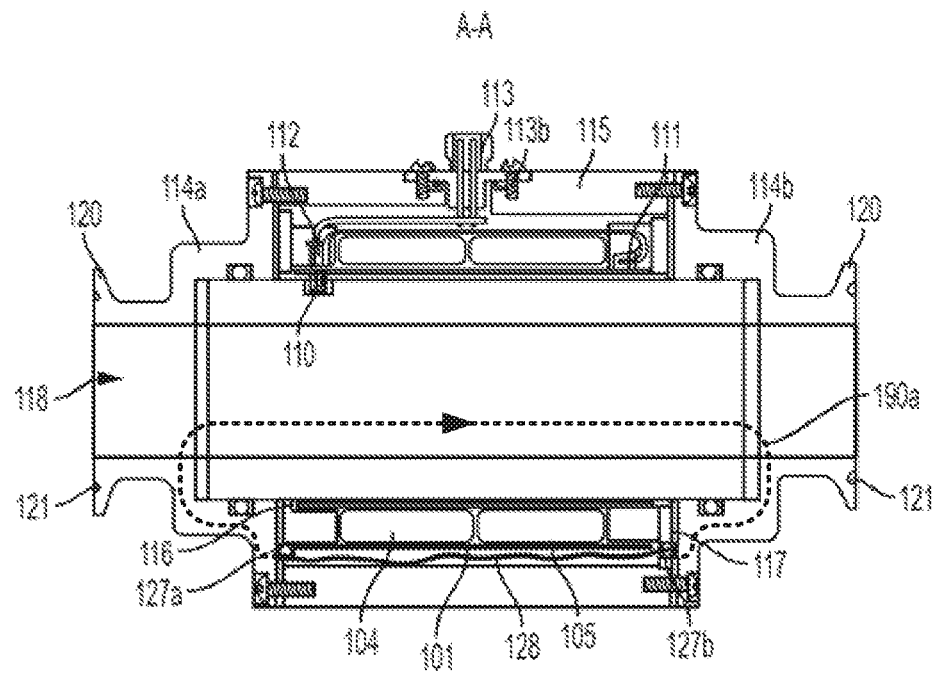
FIGS. 3A and 3B show cross-sectional views of the sensor of FIGS. 2A and 2B, taken along the lines A-A and B-B, respectively, in FIG. 2B.
Figure 3B:
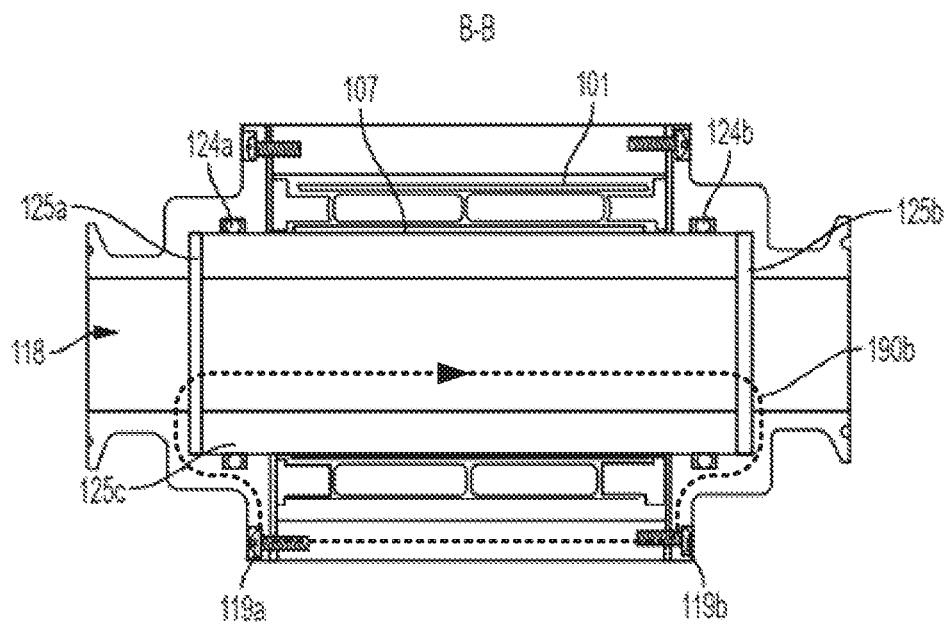

FIGS. 3A and 3B show cross-sectional views of the sensor of FIGS. 2A and 2B, taken along the lines A-A and B-B, respectively, in FIG. 2B. The sensor includes a non-conductive pipe 125c within the housing 115. As shown, the non-conductive pipe 125c and flanges 114a, 114b define a longitudinal flow path 118 through the center of the sensor 100. Flanges 114a and 114b include connections 120 for facilitating the connection of the sensor 100 in a fluid flow line. In some examples, connections 120 include a groove 121 for receiving a gasket to facilitate sealing the sensor 100 to a fluid flow line. The non-conductive pipe 125c is in fluid communication with inner openings of flanges 114a and 114b to create a flow path 118 through the sensor 100. O-ring 124a, 124b and gasket 125a, 125b can be used to seal the junctions between the non-conductive pipe 125c and flanges 114a, 114b, respectively. In some examples, the inner diameter of the non-conductive pipe 125c is approximately the same as the inner diameter of an adjacent fluid flow vessel to which the sensor 200 is attached via a connection 120. Thus, incorporating the sensor 200 into the flow path in a fluid flow system will have minimal impact on the fluid flow.

The sensor of FIG. 3A includes an excitation toroid coil 104 and a measuring toroid coil 105 similar to those discussed above with reference to FIG. 1. The excitation 104 and measuring 105 toroid coils are positioned to encircle the non-conductive pipe 125c so that fluid flowing through the sensor 100 flows through the center of the toroid coils 104, 105. The sensor 100 further includes a controller board 101 configured to interface with the toroid coils 104, 105, such as described with respect to FIG. 1. In some embodiments, the controller board 101 comprises a flexible printed circuit board (PCB) material. The controller board including components such as the controller 102, driver 103, and detector 106 of FIG. 1 can be flexibly wrapped around portions of the sensor 100 so as to be contained within the housing 115. In the illustrated embodiment, the controller board 101 is wrapped around toroid coils 104, 105 and is capable of interfacing therewith, for example, via driver 103 and detector 106, respectively. In some embodiments, toroid coils 104, 105 are soldered or otherwise electrically coupled to the driver 103 and detector 106 of the controller board, respectively.

During an exemplary conductivity sensing operation, the excitation toroid coil 104 can cause an alternating current to flow through the fluid, which can cause an alternating magnetic field to develop in the measuring toroid coil 105. In some embodiments, flanges 114a, 114b can be made of an electrically conductive material and/or may include conductive elements such that the flanges 114a, 114b are in electrical communication with fluid at the ends of the non-conductive pipe 125c. In some embodiments, the housing 115 can be made from conductive materials such as metals, alloys, or conductive plastics, and screws 119a and 119b can provide electrical communication between the housing 115 and flanges 114a and 114b, respectively. For instance, an exemplary conductive current loop can include the fluid in flow path 118, flange 114a, screw 119a, housing 115, screw 119b, and flange 114b as illustrated by loop 190b in FIG. 3B. As mentioned elsewhere herein, in some examples, sensor 100 includes a plurality of screws or other fasteners disposed about the perimeter of flanges 114a, b. In some such examples, one or more of such fasteners can contribute to the conductive path illustrated by loop 190b.

In some embodiments, the housing 115 is made from a non-conductive material, such as a glass reinforced plastic, for example. In some such embodiments, the sensor 100 includes a loop circuit wire 128 running outside of the toroid coils 104, 105, and in electrical communication the fluid at the ends of the non-conductive pipe 125c for completing a current loop with the fluid. The loop circuit wire 128 can be held in place, for example, via set screws 127a and 127b threaded into flanges 114a and 114b, respectively. In some such examples, an induced current can flow through the fluid and through the loop circuit wire 128 as illustrated by exemplary current path 190a. An induced current in the measuring toroid coil 105 indicative of the current flowing through the fluid, and the conductivity of the fluid, can be measured. In some embodiments, the sensor 100 includes other conducting elements instead of or in addition to loop circuit wire 128 to complete the current loop with the fluid for performing conductivity measurements. For example, in some embodiments, the flanges 114a, 114b can be can be secured with metal threaded rods extending through the housing 115 or other components in order to complete the current loop with the fluid flowing through the pipe 125c.

In some instances, bubbles or foam in the fluid within the flow path 118 in the sensor 100 can affect the current flowing through the sample and/or the current detected via the measuring toroid coil 105 even if the actual conductivity of the fluid does not change. That is, even though the presence of air in the fluid generally does not affect the conductivity of the fluid itself, it can impact the measured conductivity. Measuring the conductivity of the fluid containing air in the form of foam and/or bubbles may inadvertently result in including the air in the conductivity measurement. The presence of air often lowers the measured conductivity even though the true conductivity of the fluid is unaffected.

The presence of air in the form of bubbles and/or foam can affect other properties of the fluid in addition to the measured conductivity. For example, bubbles and/or foam in the flow path 118 can be dielectrically different than the fluid and can affect the dielectric properties of the fluid flowing through the pipe than would be if only the fluid were flowing. Accordingly, a measured capacitance that is affected by the fluid in the pipe can also be affected by air present in the fluid flowing therethrough. Thus, monitoring such a capacitance can indicate the presence and/or amount of bubbles and/or foam in the fluid flow path 118. In some embodiments, this can be used predict the effect of the bubbles and/or foam on the measured conductivity measurement to compensate for the bubbles and/or foam.

In some examples measuring the capacitance can include applying an electrical potential between the first capacitance electrode and the second capacitance electrode, flowing the fluid sample through the electric field between the first and second capacitance electrodes, and measuring the capacitance between the first and second capacitance electrodes. In some such examples, the conductivity measurement can determine a measured conductivity of the fluid that is flowing between the first and second capacitance electrodes. In such a configuration, the conductivity measurement and the capacitance measurement are affected by the same portion of fluid flowing through the sensor. Alternatively, in some examples, the electrodes used to measure a capacitance affected by the fluid flowing through the sensor and the coils for measuring the conductivity of the fluid can be offset longitudinally along the sensor by a known distance. In some such embodiments, a known fluid flow rate (e.g., via a flow meter in communication with the controller 102), can be used to determine a temporal offset between a conductivity measurement and a capacitance measurement affected by a particular volume of fluid. A corresponding delay in determining the measured conductivity and the measured capacitance affected by the fluid results in the capacitance and conductivity of approximately the same volume of fluid being analyzed, but at separate locations and separate times. In various such embodiments, the conductivity measurement of a volume of fluid is performed prior to performing the capacitance measurement affected by the volume. In other embodiments, the capacitance measurement affected by a volume of fluid is performed prior to the conductivity measurement of the volume.

Figure 4:
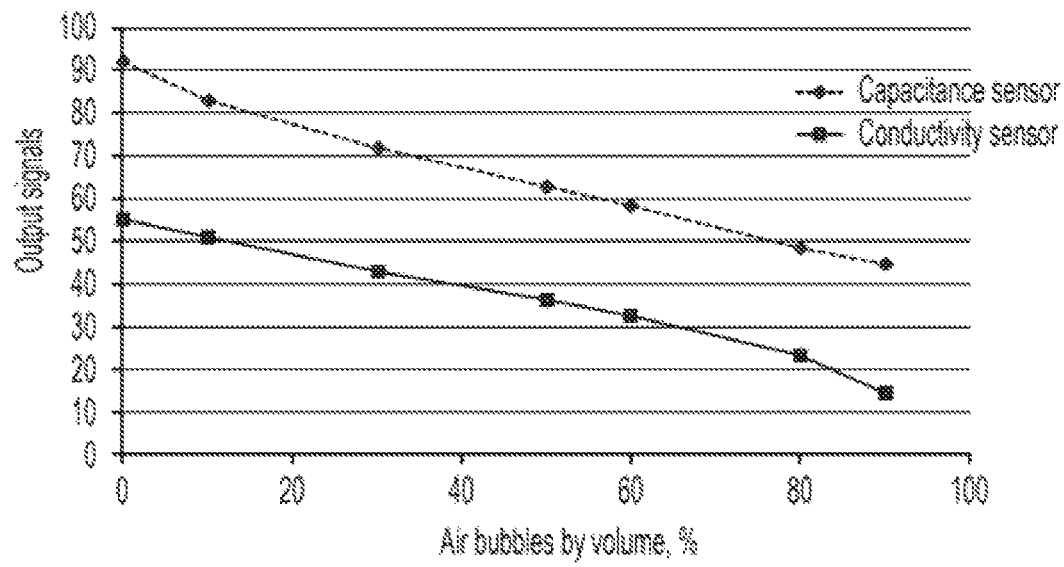
FIG. 4 is an exemplary plot showing the variation of the sensed capacitance and the sensed conductivity of fluid flowing through a pipe as the percent air by volume of the fluid changes.
Figure 5:
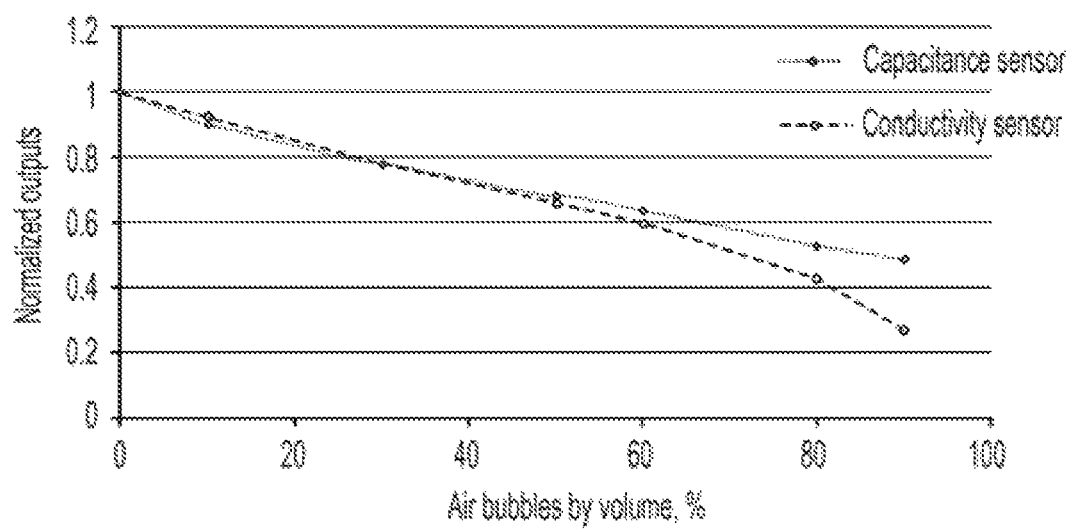
FIG. 5 is an exemplary plot showing the variation of the sensed capacitance and the sensed conductivity of fluid flowing through a pipe.

FIG. 4 is a plot showing the variation of the sensed capacitance and the sensed conductivity of fluid flowing through the pipe 125*c* as the percent air by volume of the fluid changes. In the example of FIG. 4, both the capacitance and the measured conductivity of the fluid decrease with increasing air percentage. FIG. 5 is a plot showing the variation of the sensed capacitance and the sensed conductivity of fluid flowing through the pipe 125*c*. In the plot of FIG. 5, both the capacitance and the conductivity sensor output values are normalized to a predetermined value (e.g., 1.00) at 0% air bubbles in the flow path.

Figure 6:
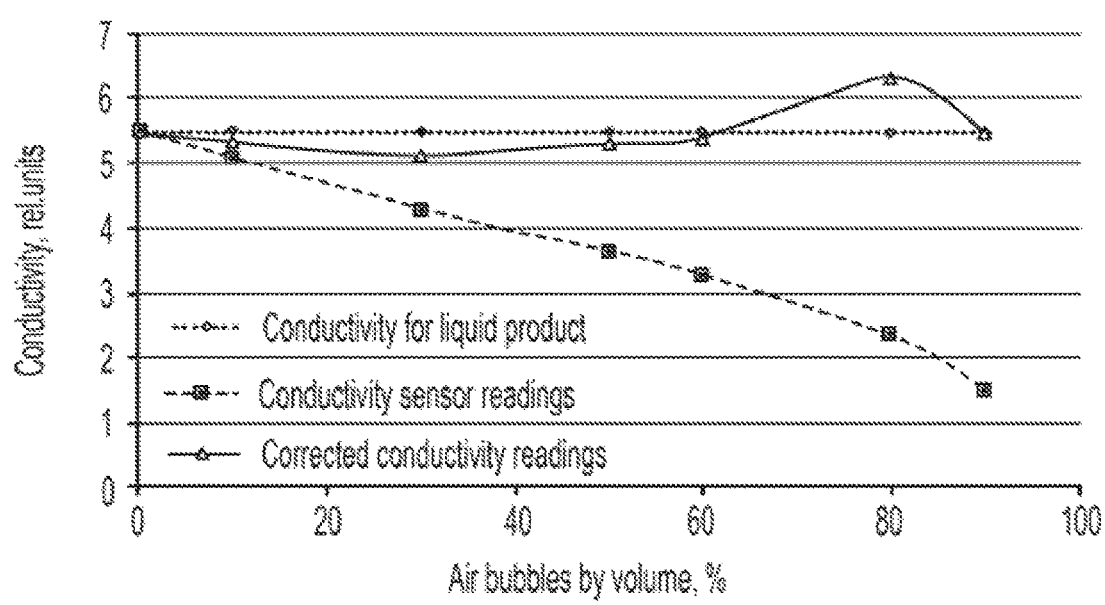
FIG. 6 is a plot showing, for a variety of air bubble concentrations within a fluid, an actual conductivity of the fluid, a measured conductivity of the fluid, and a corrected conductivity measurement.

Data from one or both of FIGS. 4 and 5 can be used to determine a correlation between the measured capacitance and the effect of the air content of the fluid on the measured conductivity. FIG. 6 is a plot showing, for a variety of air bubble concentrations within the fluid (percentage by volume), the actual conductivity of the fluid, the measured conductivity of the fluid (i.e., the conductivity sensor reading), and a corrected conductivity measurement. As shown, the conductivity of the fluid itself does not change with increasing percentage of air content, however, the conductivity sensor readings incorrectly decrease as the air content increases.

Based on a known behavior of a capacitance affected by the fluid as the air content of the fluid varies (e.g., FIGS. 4 and 5), a corrected conductivity sensor reading can be determined. For example, the controller can determine a capacitance affected by the fluid and the measured conductivity of the fluid based on received signals. Using the measured capacitance and the measured conductivity, the controller can determine the corrected conductivity measurement. In various examples, the controller can determine the corrected conductivity measurement based on an equation using the measured capacitance and conductivity as input variables. Additionally or alternatively, the corrected conductivity measurement can be determined via a lookup table stored in a memory that is a part of or otherwise in communication with controller 102.

In some examples, a measured temperature, for example, data from temperature sensor 110 can be used in determining the corrected conductivity measurement. For instance, the temperature of the fluid can affect how the capacitance and/or the conductivity measurement are affected by the presence of air in the flow path. Thus, in some examples, a lookup table or equation used for determining the corrected conductivity measurement can utilize temperature data in addition to the measured conductivity and capacitance.

In some instances, the relationship between the fluid temperature and/or the amount of air in the flow path and the capacitance and/or the measured conductivity is dependent on the fluid flowing in the system. In some embodiments, different equations and/or lookup tables can be used to determine the corrected conductivity measurement based on the fluid flowing through the system. In some embodiments, the sensor is in communication with a user interface allowing a user to identify the fluid flowing through the system. In some examples, the user interface allows a user to select the fluid from a list of fluids. The controller can then use the received selection to determine the appropriate lookup table and/or equation to use when determining a corrected conductivity measurement. In various embodiments, selecting the fluid can include selecting a particular solution and/or a constituent present in the fluid flowing through the system.

In some examples, the sensor is factory calibrated to determine corrected conductivity measurement based on received inputs such as those described elsewhere herein. In other examples, a user can perform a calibration step of flowing a fluid with a known air volume percentage (e.g., 0% air) through the sensor operating in a calibration mode. The sensor can then measure the conductivity of the fluid and utilize the user measured conductivity data with factory calibration parameters to calibrate the conductivity sensor over a range of fluid/air percentages. Similarly, one or more capacitance measurements (e.g., at 0% and 100% air by volume) can be used (with or without factory calibration values) to calibrate the capacitance measurement over a range of fluid/air percentages. Such calibration data can be combined to define a relationship (e.g., an equation or lookup table) to determine a corrected conductivity measurement for any measured conductivity and capacitance.

As described with respect to FIG. 1 above, the sensor 100 can include a sensor board 107 in communication with a controller on the controller board 101. The sensor board 107 can include electrodes 108, 109 that can be used to determine properties of the fluid in the pipe 125*c*. For example, in some embodiments, first 108 and second 109 electrodes are positioned on the sensor board so that the fluid in the flow path 118 flows between the electrodes. The fluid flowing through the flow path 118 can act as a dielectric between the electrodes, thereby affecting the capacitance therebetween. Bubbles and/or foam in the flow path 118 are dielectrically different than the fluid and can affect the capacitance between the electrodes. Thus, monitoring the capacitance between such electrodes can indicate the presence of bubbles and/or foam in the fluid flow path 118, and can be used to adjust a conductivity measurement to compensate for the bubbles and/or foam.

Additionally or alternatively, the sensor 100 can include other components for measuring different parameters of the fluid flowing through the pipe 125*c*. For example, in some embodiments, the sensor board 107 includes a temperature sensor 110 positioned proximate the pipe 125*c*. The temperature sensor 110 can output a signal, for example, to controller 102, indicative of the temperature of the fluid flowing through the flow path 118. In some such examples, the controller 102 can use the temperature information to correlate the capacitance affected by the fluid to the presence of air in the fluid, such as bubbles and/or foam.

The sensor 100 of FIG. 3A includes an external connector 113 which can communicate with additional sensor or system components. In some examples, the external connector 113 is in communication with the controller board 101 via a controller board connector 112 and with the sensor board 107 via the sensor board connector 111. The external connector 113 can be in electrical communication with the excitation toroid coil 104, the measuring toroid coil 105, electrodes (e.g., 108, 109) of the sensor board 107, and/or the temperature sensor 110. The external connector can be configured to interface with an external device for communicating therewith via wired and/or wireless communication. In various embodiments, the external device can be used to monitor signals from one or more components such as electrodes 108, 109, temperature sensor 110, the measurement toroid coil 105, or the like. Additionally or alternatively, the external device can be used to control components such as the excitation toroid coil.

Figure 7:
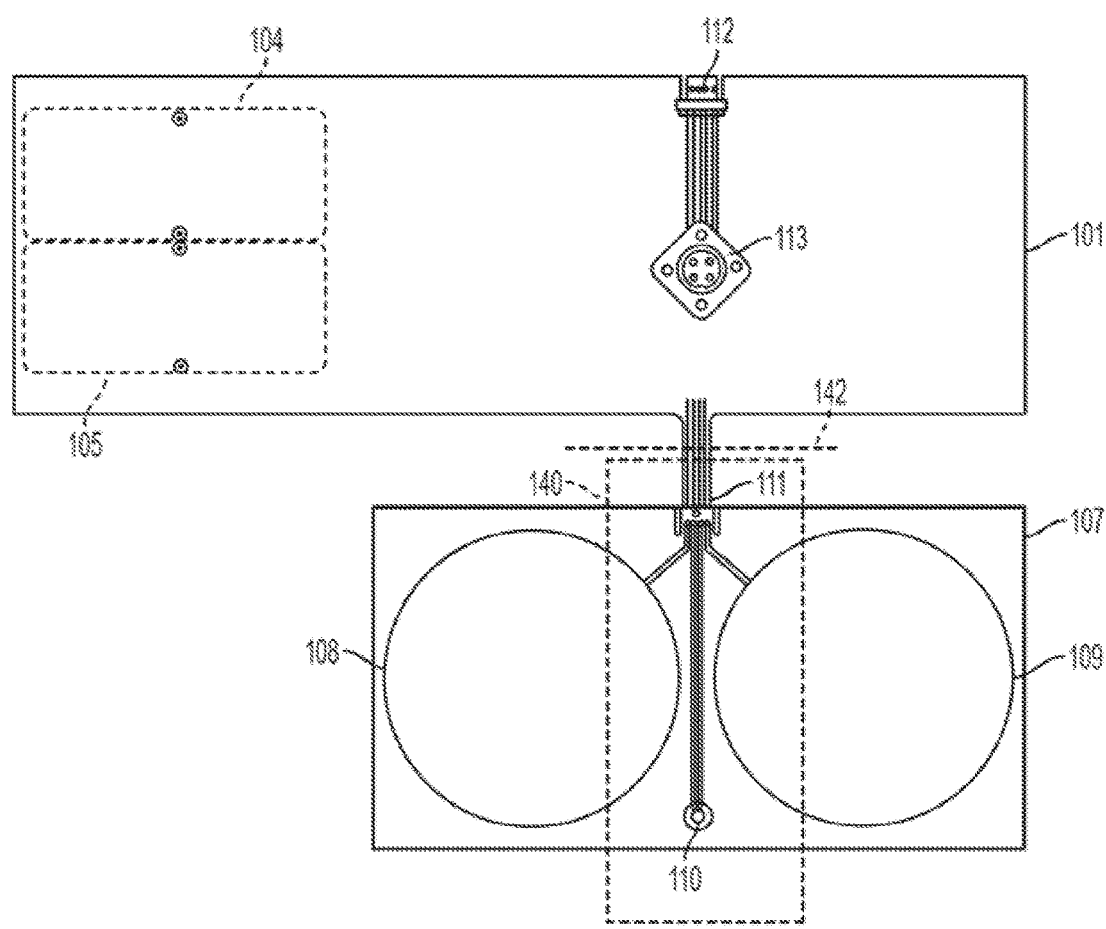
FIG. 7 shows an unrolled view of a controller board and sensor board according to some embodiments.

In some embodiments, the sensor board 107 is made from a flexible material (e.g., a flexible PCB material) that can be effectively wrapped around the non-conductive pipe 125*c* of the sensor 100. In some such embodiments, the electrodes (e.g., 108, 109) can be positioned proximate the outer surface of the pipe 125*c* about its circumference and can fit conveniently within the housing 115. FIG. 7 shows an unrolled view of a controller board and sensor board according to some embodiments. As shown, a flexible controller board 101 includes areas 104, 105 for interfacing with the excitation toroid coil and the measuring toroid coil, respectively. In some examples, the coils are soldered (e.g., from the back side shown in dashed lines) or otherwise electrically connected to the controller board 101 in areas 104, 105. The controller board 101 further includes a connector 112, which is connected to flexible connection board with an external connector 113 similar to external connector 113 as shown in FIG. 1, enabling communication with other external devices. The controller board 101 is connected to a sensor board 107 via a connector 111.

The sensor board 107 of FIG. 7 includes a first electrode 108 and a second electrode 109. In some examples, first 108 and second 109 electrodes comprise capacitance electrodes. The sensor board 107 of FIG. 7 further includes a temperature sensor 110 configured to output a signal indicative of the temperature proximate the first 108 and second 109 electrodes.

In an exemplary configuration the sensor board 107 is wrapped around a fluid flow vessel, such as the non-conductive pipe 125*c* of the sensor 100 of FIGS. 3A and 6B. The sensor board 107 can be wrapped around the pipe in approximately the orientation shown with respect to pipe 140 shown in phantom overlaid on the sensor board 107 in FIG. 7. Thus, the first 108 and second 109 electrodes are positioned such that, when the sensor board 107 is wrapped around the pipe 140, the electrodes 108 and 109 are on either side of the fluid flow path. That is, fluid flowing through the pipe will be between the electrodes 108, 109, acting as a dielectric therebetween when making capacitive measurements between the electrodes 108, 109.

After the sensor board 107 is wrapped around the pipe 140, the pipe 140 with the sensor board 107 is inserted inside the excitation toroid coil 104 and the measuring toroid coil 105. The controller board 101 can be similarly wrapped around the coils and connected to the connector 111 on the sensor board 107. Thus, similar to the cross-sectional arrangement of FIG. 3A, the pipe 125*c* is surrounded by sensor board 107, then coils 104, 105, then controller board 101.

While described with respect to FIG. 7 as being wrapped around the pipe 140, boards such as the sensor board 107 and controller board 101 need not be necessarily wrapped around the pipe 140 during construction of the conductivity sensor 100. Rather, the "unwrapped" view of FIG. 7 illustrates a possible configuration of such boards were they to be unwrapped from the conductivity sensor 100. In general, some components, such as flexible PCB boards, may be wrapped around or integrated into the pipe during construction. For instance, in some examples the pipe 140 includes a surface having electrodes 108, 109 included thereon. Controller board 101 can be configured to interface directly with such electrodes integrated onto the pipe 140.

Figure 8A:
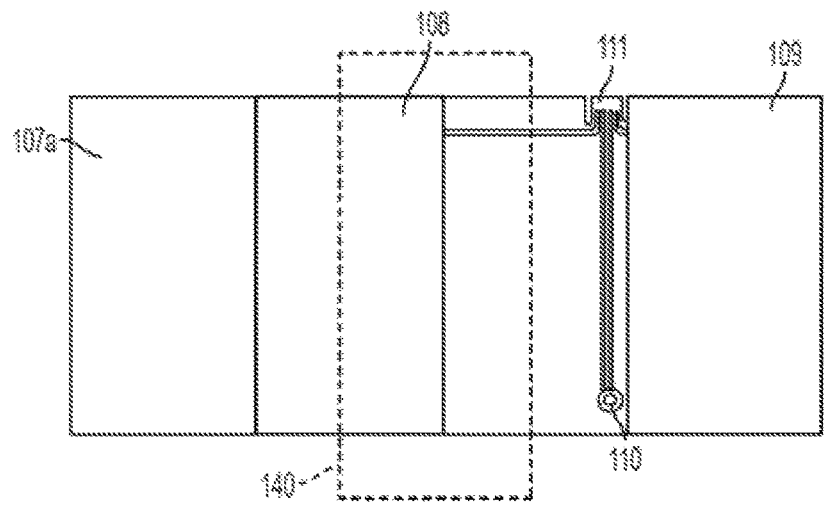
FIGS. 8A-C illustrate sensor board configurations according to various embodiments.
Figure 8B:
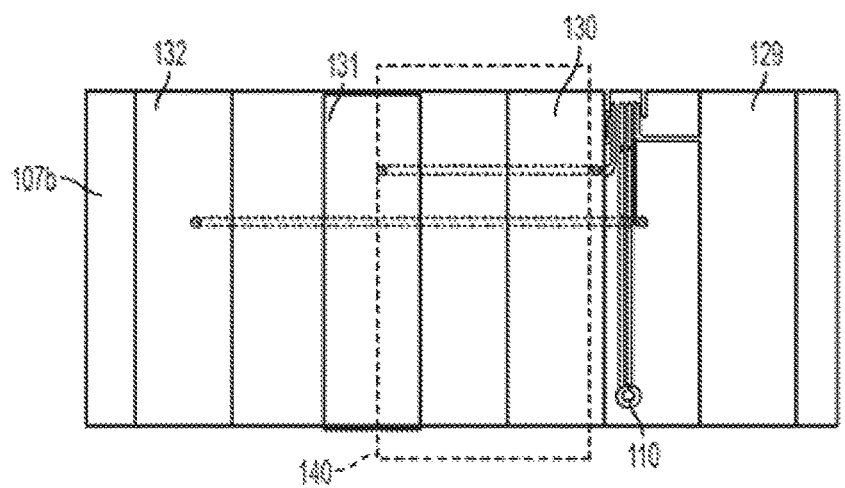
Figure 8C:
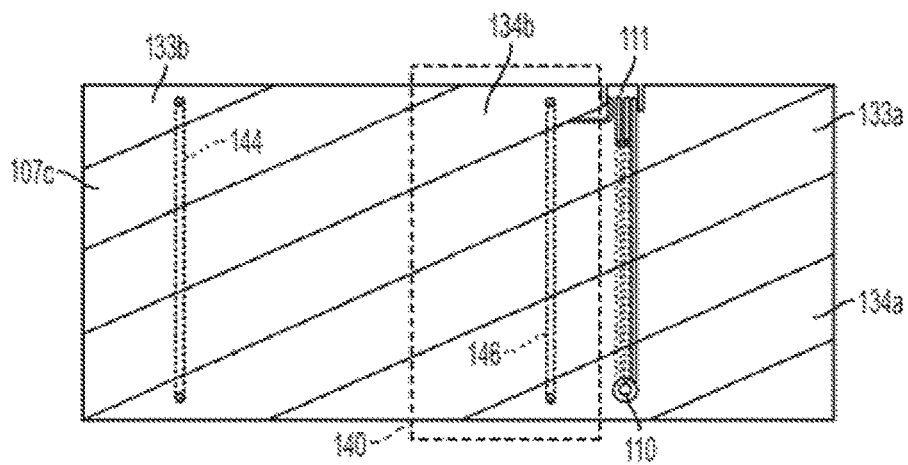

FIGS. 8A-C illustrate sensor board configurations according to various embodiments. FIG. 8A shows a sensor board 107*a* having a first electrode 108 and a second electrode 109. When wrapped around a pipe, such as insulating pipe 125*c*, electrodes 108 and 109 will be positioned on opposite sides of the pipe. For examples, with reference to FIG. 3A, the sensor board 107 at the top half of the pipe 125*c* might include the first electrode 108, while the sensor board 107 at the bottom half of the pipe 125*c* might include the second electrode 109 such that the two electrodes are positioned on opposite sides of the pipe 125*c*. The sensor board 107*a* of FIG. 8A includes a temperature sensor 110 for measuring the temperature of an area proximate electrodes 108, 109. For example, temperature sensor 110 can be used to measure the temperature of the pipe 140, which can be indicative of the temperature of the fluid flowing therethrough. The electrodes 108, 109 and/or the temperature sensor can be electrically connected to other portions of the sensor or of a fluid flow system via connector the sensor board connector 111.

FIG. 8B shows a sensor board 107*b* similar to that of FIG. 8A, and including more electrodes. The sensor board 107*b* of FIG. 8B includes a first electrode 129, a second electrode 130, a third electrode 131, and a fourth electrode 132. When wrapped around a pipe 140, first 129 and third 131 electrodes will be positioned opposite one another with the fluid path extending therebetween. Similarly, when the sensor board 107*b* is wrapped around pipe 140, the second 130 and fourth 132 electrodes will also be positioned opposite one another with the fluid path extending therebetween. The four electrodes 129, 130, 131, and 132 spaced about the perimeter of the pipe can allow for a variety of capacitive measurements to be performed, such as capacitive measurements between any two electrodes. In some examples, the plurality of electrodes can be used for performing electrical capacitance tomography processes. Similarly to the sensor board 107*a* of FIG. 8A, the sensor board 107*b* of FIG. 8B includes a sensor board connector 111 for facilitating electrical communication between portions of the sensor board 107*b* and other sensor or system components. As shown, each of electrodes 129, 130, 131, and 132 is connected to the connector 111. The sensor board 107*b* further includes a temperature sensor 110 in communication with the connector 111.

FIG. 8C shows a sensor board 107*c* configured to provide helical electrodes surrounding a pipe. The sensor board 107*c* of FIG. 8C includes four electrodes: 133*a*, 133*b*, 134*a*, and 134*b*. When wrapped around a pipe 140, the left edge of electrode 133*b* will approximately meet the right edge of electrode 133*a*, while the left edge of electrode 134*b* will approximately meet the right edge of electrode 134*a*, forming a double-helix shape. That is, electrodes 133*a* and 133*b* form a first helix and electrodes 134*a* and 134*b* form a second helix intertwined with the first. As shown, a first connection 144 can be used to electrically couple electrode 133*a* and electrode 133*b*, and a second connection 146 can be used to electrically couple electrode 134*a* and electrode 134*b*. Thus, each of the helixes forms essentially a single electrode wherein, at any length of the pipe covered by sensor board 107*c*, one helix is positioned approximately across from the other, with the fluid flow path positioned therebetween. A capacitance measurement between one helix (e.g., electrodes 133*a*, 133*b*) and the other helix (e.g., electrodes 134*a*, 134*b*) can be used to determine properties of the fluid in the pipe 140. Similarly to the sensor boards in FIGS. 8A and 8B, sensor board 107*c* of FIG. 8C includes a sensor board connector 111 for facilitating electrical communication between portions of the sensor board 107*c* and other sensor or system components. As shown, each of electrodes 133a and 134b (and thus, each of the helixes) are connected to the connector 111. The sensor board 107c further includes a temperature sensor 110 in communication with the connector 111. Thus, each of the helical electrodes (133a, b and 134a, b) and the temperature sensor 110 can be in electrical communication with the controller board via the connector 111.

In general, while components such as the sensor board and controller board are described as being "wrapped" around various components such as the pipe 125c, such language is used in conjunction with the "unwrapped" views of such boards in FIGS. 7 and 8A-8C. In in some examples, such boards are separately constructed components, for example, on a flexible PCB board, that are physically wrapped around the pipe 125c during assembly. In other embodiments, a board such as the sensor boards of FIGS. 7 and 8A-8C may be incorporated into the surface of the pipe 125c. For example, electrodes such as 108 and 109 or other board elements can be printed onto or otherwise applied to the pipe 125c and be connected to the controller board via a connector 111 positioned proximate the pipe 125c. FIGS. 7 and 8A-8C provide "unwrapped" views of such electrodes for clarity and ease of description even if the sensor board features cannot physically be unwrapped from the pipe 125c according to some embodiments.

In general, any of the sensor boards of FIGS. 8A-C can be used as sensor board 107 as shown in FIGS. 3A and 3B. With reference to FIGS. 1 and 3A, the sensor board 107 can be used to measure various properties of a fluid flowing through the pipe 125c, such as, for example, dielectric properties of the fluid via a capacitance measurement or the temperature of the fluid using the temperature sensor 110. During exemplary operation of the sensor 100, the controller 102 can cause a current to be applied to the excitation toroid coil 104, for example, via the driver 103. The controller 102 can receive a signal from the measuring toroid coil 105, for example, via detector 106. The received signal can be used to determine a conductivity of the fluid flowing through the pipe 125c.

As described above with respect to FIGS. 8A-C, while the fluid is flowing through the pipe 125c, the fluid is generally flowing between electrodes of the sensor board 107. The controller 102 can be configured to determine the capacitance between such electrodes (e.g., 108, 109) on the sensor board 107. The determined capacitance can be impacted due to the composition of the fluid in the pipe 125c. In some embodiments, the controller can use the measured capacitance of the fluid to determine the effect of the air in the pipe 125c on the conductivity measurement. The controller can determine a corrected conductivity based on the initial conductivity measurement, the capacitance measurement, and, in some instances, a temperature measurement.

Figure 9:
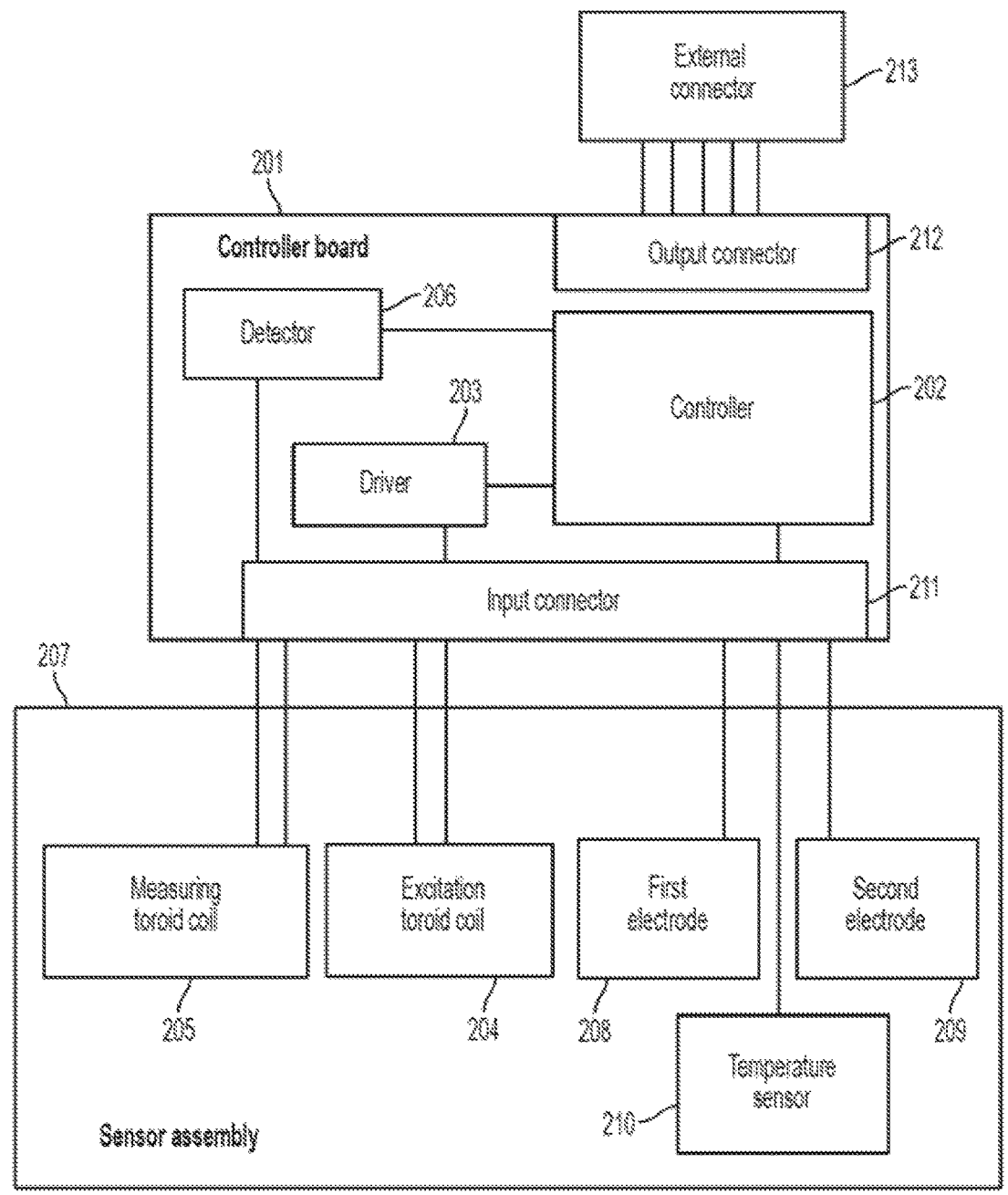
FIG. 9 is a block diagram illustrating an exemplary conductivity sensor having a sensor assembly.

The sensor of FIGS. 2 and 3 is shown as being connectable between sections of pipe in a fluid flow system (e.g., via clamp connection 120). Additionally, various portions of the sensor are disposed outside of the fluid flow vessel (i.e., flow path 118 through pipe 125c). Alternatively, in some embodiments, the sensor can include a sensor assembly that can be immersed in a fluid flow path in an existing flow system. FIG. 9 is a block diagram illustrating an exemplary conductivity sensor having a sensor assembly. As shown, sensor 200 includes a controller board 201, a sensor assembly 207, and an external connector 213. In some examples, sensor assembly 207 is immersible in fluid flowing through a system. The sensor assembly 207 includes an excitation toroid coil 204 and a measuring toroid coil 205, a first electrode 208, a second electrode 209, and a temperature sensor 210. The controller board 201 includes a controller 202 in communication with the excitation toroid coil 204 via a driver 203, and with the measuring toroid coil 205 via a detector 206. As described elsewhere herein, the controller 202 can interface with the excitation 204 and measuring 205 toroid coils to perform a conductivity measurement of fluid flowing through the toroids. In addition, the controller can be in communication with the first 208 and second 209 electrodes and the temperature sensor 210 via an input connector 211. Additionally or alternatively, in some embodiments, input connector 211 can be configured to facilitate communication between the detector 206 and the measuring toroid coil 205 and between the driver 203 and the excitation toroid coil 204.

The controller 202 can interface with electrodes to measure a parameter affected by the fluid flowing in the system, such as a capacitance. Moreover, as described elsewhere herein, the controller can interface with toroid coils and electrodes to determine a measured conductivity and a measured capacitance. The controller 202 can, based on the received data, and in some examples, temperature data from temperature sensor 210, determine a corrected conductivity measurement to compensate for the presence of air flowing through the system (e.g., bubbles, foam, etc.). The controller board 201 includes an output connector 212 in communication with an external connector 213. In some examples, the controller can output various information, such as signals received from various components and/or the determined corrected conductivity measurement, to other system components, such as a computer, smartphone, tablet, and the like. In some embodiments, output connector 212 and/or external connector 213 can be capable of wired communication, wireless communication, or both.

Figure 10A:
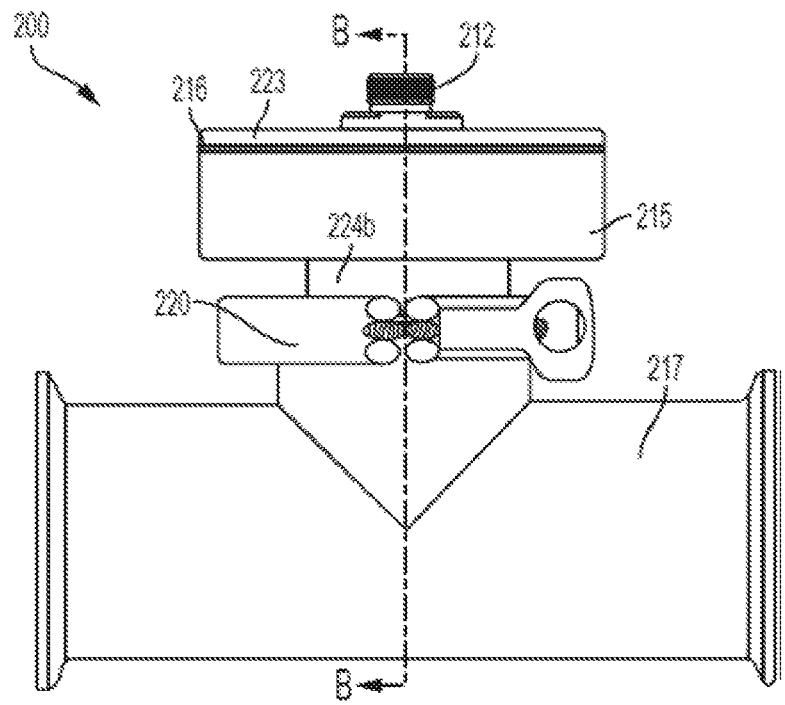
FIGS. 10A and 10B are view of a sensor positioned within an existing flow system.
Figure 10B:
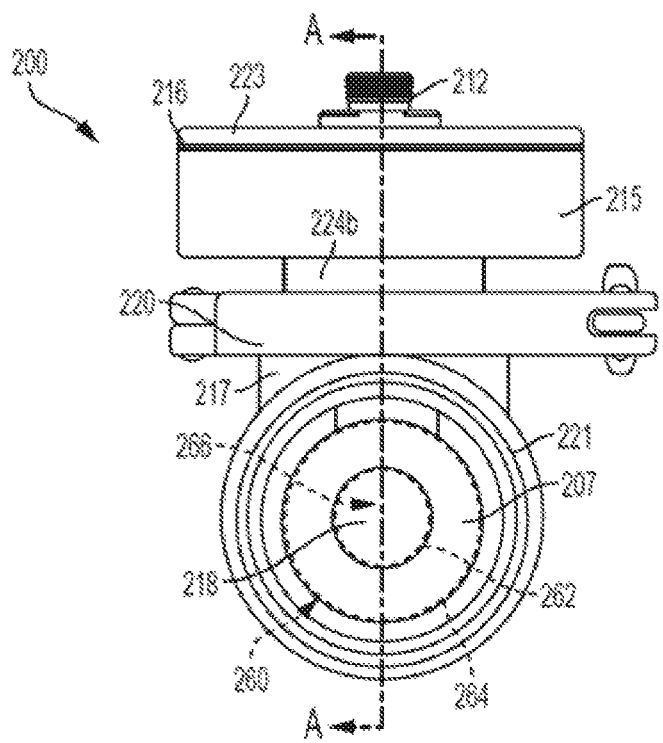

FIGS. 10A and 10B are view of a sensor positioned within an existing flow system. Referring to FIG. 10A, in the illustrated embodiment, the sensor 200 is coupled to a tee pipe 217. While the tee pipe 217 of FIG. 10A is shown as being separate from and attachable to fluid flow systems, in some examples, the sensor 200 can be inserted into a tee pipe 217 existing in a fluid flow system and having an open port. Thus, use of the sensor 200 would not require breaking any connections between system components, allowing for easier installation and removal without major system destruction.

As shown, the sensor 200 is coupled to the tee pipe 217 via clamp 220. While shown as interfacing with the tee 217 via a clamp 220, in various embodiments, the sensor 200 can be configured to engage the tee 217 via any of a variety of known fluid system connections. The sensor 200 includes a controller box 215 having a cover 223. In the illustrate embodiment, the sensor 200 includes a controller box gasket 216 to create a seal between the box cover 223 and the controller box 215.

As discussed with respect to FIG. 9, the sensor 200 of FIG. 10 includes an output connector 212 which can be used to facilitation of communication between a controller of the sensor and an external device. In some examples, the output connector 212 is a specific type of connector configured to interface with a particular wire or other system component to facilitate communication between the controller and other devices.

FIG. 10B is a side view of the sensor of FIG. 10A. The side view of the sensor 200 shown in FIG. 10B shows a view through the tee pipe 217. As shown, the sensor assembly 207 protrudes into the tee, extending to the section through which fluid flows. The sensor assembly 207 includes a housing 260 that can protect components of the sensor assembly 207 within the housing 260 from fluid flowing through the tee 217. In some embodiments, the housing 260 is an annular housing. The annular housing can include an inner surface 262 and an outer surface 264. The inner surface 262 defines an aperture 266 extending longitudinally through the sensor 200. At least some of the fluid flowing through the tee 217 flows through the aperture 266 of the sensor 200, and thus the aperture 266 forms the flow path 218 for the fluid flowing through the sensor 200.

Figure 11A:
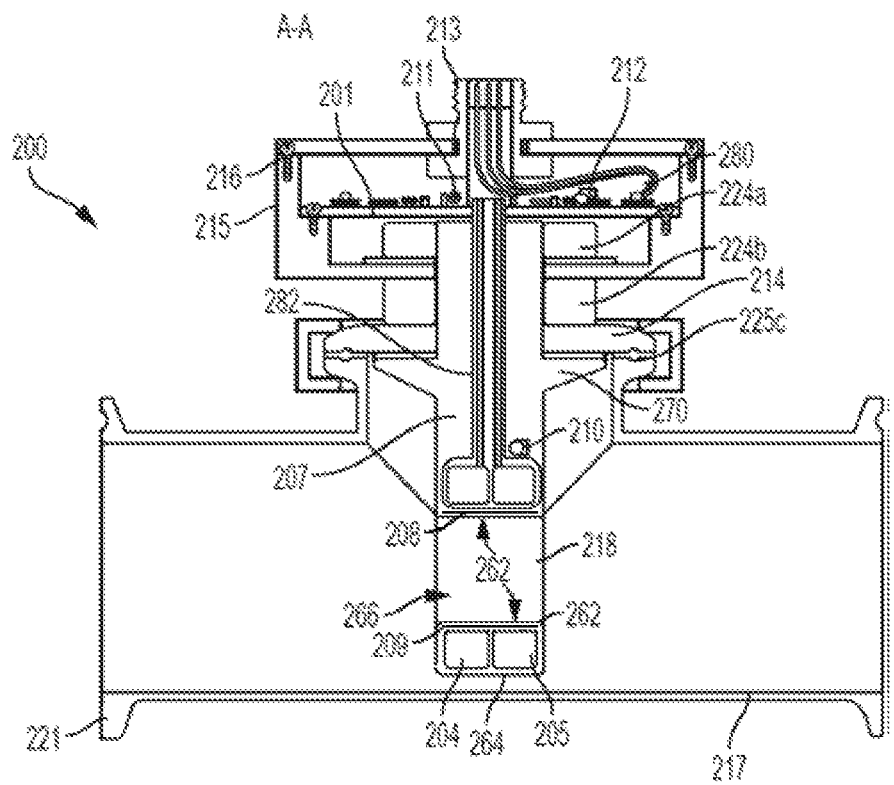
FIGS. 11A and 11B are cross-sectional views of the sensor of FIGS. 10A and 10B positioned within a tee pipe, taken along lines A-A and B-B, respectively, in FIG. 10B.

FIG. 11A is a cross-sectional views of the sensor of FIGS. 10A and 10B positioned within a tee pipe, taken along line A-A in FIG. 10B. The sensor 200 includes a controller box 215 housing a controller board 201 such as the controller board described with respect to FIG. 9. As shown, the external connector 213 is coupled internally to wires 280 extending from the external connector 213 to the output connector 212 of the controller board 201. The controller board 201 includes an input connector 211 shown as connected wires 282 from the controller board 201 to the sensor assembly 207. The controller box 215 is secured to the sensor assembly 207 via nuts 224a, 224b. As shown, a portion of the controller box 215 is held in place by nuts 224a, 224b threaded onto a portion of the sensor assembly 207. While shown as being threadably engaged with the sensor assembly 207 in FIG. 11A, nuts 224a, 224b can include alternative forms of attachment. For instance, nuts 224a, 224b can be secured to the sensor assembly 207 by a friction fit or other forms of attachment.

The sensor 200 of FIG. 11A further includes a flange 214 for engaging a corresponding flange of the tee pipe 217. In some examples, a gasket 225c between the respective flanges prevents fluid from leaking from the junction between the sensor 200 and the tee pipe 217. Clamp 220 can be used to secure the respective flanges to one another. Nut 224b can secure the flange 214 in place relative to the sensor assembly 207. In some examples, nut 224b secures the flange 214 to a fixed portion 270 of the sensor assembly 207.

As shown, a portion of the sensor assembly 207 protrudes into the tee pipe 217. The sensor assembly 207 includes an outer surface 264 and an inner surface 262 defining an aperture 266 serving as a flow path 218 for fluid flowing through the sensor 200 in the tee pipe 217. In the illustrated embodiment, the sensor assembly 207 includes an excitation toroid coil 204 and a measuring toroid coil 205, each surrounding the inner surface 262 and being contained within the outer surface of the housing. Such coils 204, 205 can be in communication with the controller on the controller board 201 via, for example, wires 282 and input connector 211. As described elsewhere herein, the controller can interact with coils 204, 205 to determine a measured conductivity of the fluid flowing through the flow path 218 through the aperture 266.

The sensor assembly 207 of FIG. 11 further includes a first electrode 208 and a second electrode 209 positioned between the coils 204, 205 and the inner surface 262 of the housing, and on opposite sides of the aperture 266. The electrodes 208, 209 can be in communication with the controller on the controller board 201 via wires 282 and input connector 211. As described elsewhere herein, the controller can use electrodes 208, 209 to measure a capacitance affected by the fluid flowing through flow path 218. The capacitance between the first electrode 208 and the second electrode 209 can be measured and use to adjust the measured conductivity to determine a corrected conductivity measurement.

The sensor 200 of FIG. 9 includes a temperature sensor 210 disposed in the sensor assembly 207 of the sensor 200. Temperature sensor 210 is positioned proximate the interface of the fluid with the sensor assembly 207, and can be used to determine the temperature of the fluid being analyzed in the flow path 218. Information from the temperature sensor 210 can be communicated to the controller on the controller board 201 via wires 282 and input connector 211. In some examples, the controller can use data from the temperature sensor 210 in determining the corrected conductivity measurement. That is, in some examples, the controller receives a measured conductivity value, a measured capacitance, and a measured temperature. Via an equation or a lookup table stored in a memory, the controller can determine a corrected conductivity measurement based on the received values, the corrected conductivity measurement accounting for the presence of air (e.g., bubbles, foam, etc.) in the flow path 118 of the sensor 200.

Figure 11B:
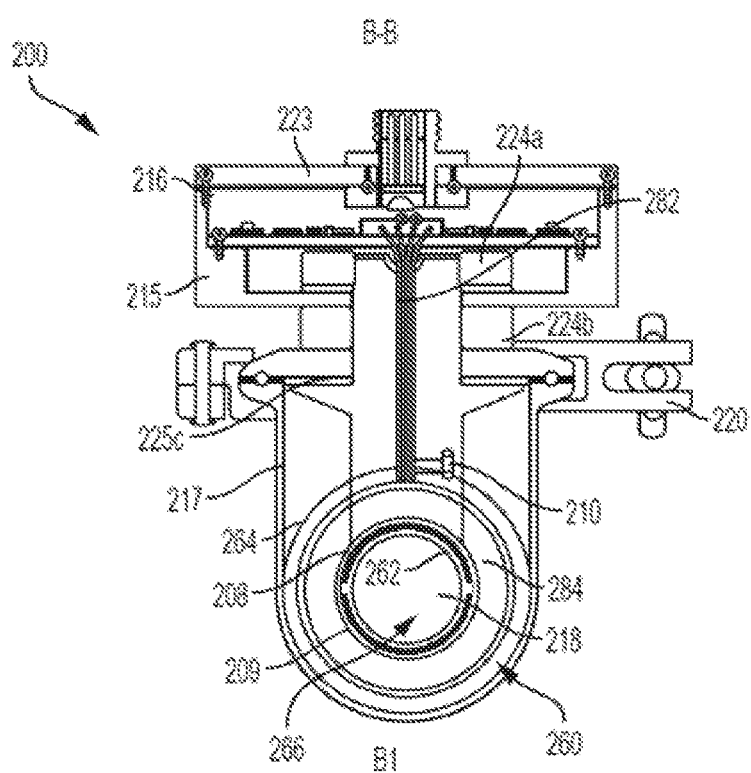

FIG. 11B is a cross-sectional views of the sensor of FIGS. 10A and 10B positioned within a tee pipe, taken along line B-B in FIG. 10A. As shown in FIG. 11A, the sensor 200 includes a sensor assembly 207 having a portion extending into the flow path of the tee pipe 217. As shown, the sensor assembly includes an annular housing 260 having an inner surface 262 and an outer surface 264, the inner surface 262 defining an aperture 266. The aperture 266 can form a flow path 218 through which fluid flows when being analyzed by the sensor 200. The view of FIG. 11B shows a coil 284 surrounding the inner surface 262 of the housing 260 and being contained within the outer surface 264. The sensor 200 includes a first electrode 208 and a second electrode 209 positioned on either side of the aperture 266 and between the coil 284 and the inner surface 262 of the housing 260. Thus, electrodes 208, 209 can be used to measure a capacitance that is affected by the fluid flowing through the flow path.

As shown, the first 208 and second 209 electrodes warp partially around the inner surface 262 of the housing 260. In some examples, first 208 and second 209 electrodes are arranged on a flexible board, similar to electrodes 108, 109 in FIG. 7, that is wrapped around the inner surface 262 of the housing 260. In various embodiments, first 208 and second 209 electrodes can be formed on a flexible board such as any of the sensor boards illustrated in FIGS. 8A-8C. Such a flexible board can be separate from and physically wrapped around the inner surface 262 of the housing 260. Alternatively, in some examples, electrodes such as those formed by wrapping the sensor boards of FIGS. 8A-8C around (i.e., helical electrodes, a plurality of rectangular electrodes, etc.) can be formed directly on the inner surface 262 of the housing 260.

During exemplary operation of a sensor such as those described herein, a sensor is positioned in a flow path of a fluid flow system. This can include breaking the flow path of a fluid flow system and inserting a sensor such as sensor 100 of FIGS. 1-3 between fluid flow vessels, such as via flanges on either side of the sensor, to create a continuous flow path through the flow vessels of the system and the sensor. Alternatively, positioning the sensor can include placing the sensor in an existing flow path, for example, via an open port of a tee pipe, such as shown in FIGS. 9-11.

In some such embodiments, once the sensor is in place in the system, fluid flowing through the fluid flow system flows through an annular housing (e.g., 260). A controller (e.g., 102, 202) in communication with a conductivity sensor (e.g., an excitation toroid coil and measuring toroid coil) can be configured to determine a measured conductivity of the fluid. It will be appreciated that other conductivity sensors apart from toroidal sensors are possible for measuring a determined conductivity.

The controller is further in communication with at least two electrodes (e.g., 108, 109) positioned such that the fluid flowing through the annular housing affects the capacitance between the electrodes. The controller can be used to measure the capacitance between the electrodes while fluid is flowing through the pipe. In some examples, the controller interfaces with the electrodes and the conductivity sensor in order to measure the conductivity of the fluid and a capacitance affected by the fluid substantially simultaneously. In some examples, the sensor further includes a temperature sensor in communication with the controller such that the controller can determine a measured temperature of the fluid flowing through the sensor.

The controller can be configured to determine a corrected conductivity measurement based on the received and determined information, such as the measured conductivity of the fluid, the measured capacitance affected by the fluid, and the temperature of the fluid. In some examples, the corrected conductivity measurement can account for the presence of air (e.g., foam and/or bubbles) in the fluid that affects the original conductivity measurement. In various embodiments, the controller can be in communication with a memory that includes a lookup table and/or an equation for determining the corrected conductivity measurement based on a plurality of received inputs. In addition to inputs such as a measured conductivity, measured capacitance, and temperature, the controller can receive additional inputs, such as via a user interface. In some such examples, a user may input one or more parameters used in determining the corrected conductivity measurement, such as a sample type or a chemical constituent of the fluid sample.

Such sensors can be in communication with other aspects of the fluid flow system. For example, in various embodiments, the controller can communicate with system equipment to effect a change in system operation based on a corrected conductivity measurement. Such changes can include, for example, changing the flow rate of a fluid or of a constituent being added to the fluid, diluting the fluid, heating or cooling the fluid, and the like. Additionally or alternatively, the controller can be used to alert a technician, locally and/or remotely, based on the corrected conductivity measurement.

Some of the techniques described in this disclosure may also be embodied or encoded in a computer-readable medium, such as a non-transitory computer-readable storage medium containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), a hard disk, optical media, or other computer readable media.

Various embodiments have been described. Such examples are non-limiting, and do not define or limit the scope of the invention in any way. Rather, these and other examples are within the scope of the following claims.

The invention claimed is:

1. A system comprising:
a conductivity sensor for measuring the conductivity of at least a first portion of a fluid sample;
a first capacitance electrode;
a second capacitance electrode; and
a controller configured to
   determine a measured conductivity from the conductivity sensor;
   determine a measured capacitance between the first capacitance electrode and the second capacitance electrode; and
   determine a corrected conductivity measurement based on the measured capacitance and the measured conductivity; wherein
the first and second capacitance electrodes are positioned so that the capacitance between the first and second capacitance electrodes is affected by the first portion of the fluid sample.

2. The system of claim 1, further comprising a sensor assembly comprising:
the first and second capacitance electrodes;
an annular housing having an inner surface and an outer surface, the inner surface defining an aperture extending in the direction of fluid flow through the sensor; and
wherein the conductivity sensor comprises:
a first coil positioned in the annular housing, the first coil surrounding the inner surface of the annular housing; and
a second coil positioned in the annular housing and downstream of the first coil, the second coil surrounding the inner surface of the annular housing; wherein
the first portion of the fluid sample comprises fluid that flows through the aperture of the annular housing such that the first and second coils can be used to determine the conductivity of the first portion of the fluid sample; and
the first and second capacitance electrodes are configured to measure a capacitance that is affected by the fluid flowing through the inner surface of the annular housing.

3. The system of claim 2, wherein the first and second capacitance electrodes are positioned within the annular housing such that the first capacitance electrode is positioned on a first side of the inner surface of the annular housing, and the second capacitance electrode is positioned on a second side of the inner surface of the annular housing, the second side being opposite the first.

4. The system of claim 3, wherein at least a portion the first and at least a portion of the second capacitance electrodes are positioned between the inner surface of the annular housing and at least one of the first and second coils.

5. The system of claim 2, further comprising a flange and an attachment member, the attachment member securing the annular housing to the flange such that the flange can be secured to a fluid reservoir containing the fluid sample and the annular housing is disposed in the fluid sample.

6. The system of claim 5, wherein the flange is configured for securing the annular housing to a tee-pipe.

7. The system of claim 2, wherein the annular housing comprises
a non-conductive pipe defining the inner surface of the annular housing;
a first flange positioned on a first side of the non-conductive pipe; and
a second flange positioned on a second side of the non-conductive pipe, the second side opposite the first; wherein
the first and second flanges are configured to interface with fluid flow vessels in a fluid flow system; and
when the first and second flanges interface with respective fluid flow vessels, the annular housing and the fluid flow vessels create a continuous fluid flow path therethrough.

8. The system of claim 7, wherein a portion of outer surface of the annular housing comprises an electrically conductive material.

9. The system of claim 7, wherein the diameter of the inner surface of the annular housing defined by the non-conductive pipe is approximately the same as the inner diameter of the fluid flow vessels so that the system does not impede the flow of fluid through the system.

10. The system of claim 1, wherein the conductivity sensor measures the conductivity of the first portion of the fluid sample and the first capacitance electrode and the second capacitance electrode are used to measure a capacitance affected by the first portion of the fluid sample substantially simultaneously.

11. The system of claim 1, further comprising a user interface in communication with the controller wherein:
a user can select at least one constituent of the fluid sample via the user interface; and
determining the corrected conductivity measurement based on the measured capacitance is further based on the selected at least one constituent of the fluid sample.

12. The system of claim 1, further comprising a temperature sensor in communication with the controller, and wherein the determining the corrected conductivity measurement is further based on a measured temperature of the fluid flowing through the system.

13. A method for performing a conductivity measurement of a flowing fluid comprising:
flowing a fluid sample past a conductivity sensor;
measuring the conductivity of the fluid sample;
flowing the fluid sample past a first capacitance electrode and a second capacitance electrode;
measuring a capacitance affected by the fluid sample using the first and second capacitance electrodes;
correlating the measured capacitance with a conductivity correction; and
determining a corrected conductivity value by adjusting the measured conductivity based on the conductivity correction.

14. The method of claim 13, wherein measuring a capacitance affected by the fluid sample and measuring the conductivity of the fluid sample comprises measuring the conductivity of and a capacitance affected by approximately the same volume of the fluid sample.

15. The method of claim 14, wherein measuring the conductivity of the fluid sample comprises measuring the conductivity of a portion of the sample that is flowing between the first and second capacitance electrodes such that the conductivity of and the capacitance affected by approximately the same volume of the fluid sample are measured simultaneously.

16. The method of claim 14, further comprising
measuring the flow rate of the flowing fluid sample; and
determining a lag time between a conductivity sensor for measuring the conductivity of the fluid sample and a capacitance sensor for measuring the capacitance affected by the fluid sample based on the flow rate; and wherein
the steps of measuring the capacitance of the fluid sample and measuring the conductivity affected by the fluid sample are separated by the determined lag time.

17. The method of claim 13, further comprising:
receiving an input identifying at least one characteristic of the fluid sample; and wherein
wherein determining the corrected conductivity value comprises calculating the corrected conductivity and incorporating the at least one characteristic of the fluid sample in the calculation.

18. The method of claim 17, wherein the at least one characteristic of the fluid sample comprises a constituent in the fluid sample.

19. The method of claim 13, further comprising inserting the sensor assembly of the sensor into a tee pipe of an existing flow system and securing a flange of the sensor to a flange of the tee pipe.

20. The method of claim 13, wherein the conductivity sensor is an inductive conductivity sensor.

21. A sensor for determining the conductivity of a fluid in a fluid flow system comprising:
a sensor board made from a flexible printed circuit board (PCB) material and including a first electrode, a second electrode, a temperature sensor, and a connector, the sensor board being wrapped around a fluid flow path so that at least some of the fluid flowing in the fluid flow system flows between a portion of the first electrode and the second electrode;
an excitation toroid coil and a measuring toroid coil, the excitation and measuring toroid coils each surrounding a portion of the fluid flow path so that at least some of the fluid flowing through the fluid flow system flows through both the excitation and measuring toroid coils; and
a controller configured to:
communicate with the excitation and measuring toroid coils in order to determine a measured conductivity of the fluid flowing through the flow system;
determine the capacitance between the first and second electrodes of the sensor board;
determine the temperature of the fluid flowing through the fluid flow system; and
determine a corrected conductivity value for the fluid flowing through the fluid flow system based on the measured conductivity, the determined capacitance, and the determined temperature.

* * * * *